US010213359B2

(12) United States Patent
Banwell et al.

(10) Patent No.: US 10,213,359 B2
(45) Date of Patent: Feb. 26, 2019

(54) SCAR REDUCTION APPARATUS

(71) Applicants: i2r Medical Limited, Dorset (GB); Paul Banwell, East Sussex (GB)

(72) Inventors: Paul Banwell, East Sussex (GB); Ian James Hardman, Dorset (GB); Keith Patrick Heaton, Dorset (GB)

(73) Assignees: I2R MEDICAL LIMITED, Dorset (GB); Paul Banwell, East Sussex (GB)

( * ) Notice: Subject to any disclaimer, the term of this patent is extended or adjusted under 35 U.S.C. 154(b) by 1155 days.

(21) Appl. No.: 14/376,135

(22) PCT Filed: Jan. 29, 2013

(86) PCT No.: PCT/GB2013/050192
§ 371 (c)(1),
(2) Date: Jul. 31, 2014

(87) PCT Pub. No.: WO2013/114097
PCT Pub. Date: Aug. 8, 2013

(65) Prior Publication Data
US 2015/0032035 A1 Jan. 29, 2015

(30) Foreign Application Priority Data

Feb. 1, 2012 (GB) .................................. 1201698.6

(51) Int. Cl.
*A61H 7/00* (2006.01)
*A61H 9/00* (2006.01)
(Continued)

(52) U.S. Cl.
CPC ....... *A61H 7/001* (2013.01); *A61F 13/00068* (2013.01); *A61H 9/005* (2013.01);
(Continued)

(58) Field of Classification Search
CPC ... A61F 2013/0028; A61H 7/00; A61H 7/001; A61H 7/008; A61H 9/00; A61H 9/005; A61H 9/0057
See application file for complete search history.

(56) References Cited

U.S. PATENT DOCUMENTS 5,759,570 A * 6/1998 Arnold ................ A61F 13/0203
424/443
6,255,552 B1 7/2001 Cummings et al.
(Continued)

FOREIGN PATENT DOCUMENTS

| EP | 1578477 B1 | 9/2011 |
| WO | 2004112666 A1 | 12/2004 |
| WO | 2007041642 A2 | 4/2007 |

OTHER PUBLICATIONS

International Search Report of PCT Patent Application No. PCT/GB2013/050192 dated Apr. 26, 2013.
(Continued)

*Primary Examiner* — Michael Tsai

(57) ABSTRACT

Post-scar formation reduction apparatus comprises a biocompatible scar interface layer, a compressible pressure chamber overlying the scar interface layer, and an at least substantially uniformly compressible pressure element in the pressure chamber which extends over the scar interface layer. The pressure element has a bulk modulus enabling a predetermined uniform or substantially uniform compression of the pressure element in at least a direction perpendicular or substantially perpendicular to the scar interface layer on application of a specific pressure. Evacuator is also provided which at least partially evacuates the pressure chamber, whereby the pressure element is uniformly or substantially uniformly compressed in the direction of the
(Continued)

scar interface layer and the pressure chamber positively urges the compressed pressure element towards the scar interface layer.

16 Claims, 4 Drawing Sheets

(51) Int. Cl.
*A61M 1/00* (2006.01)
*A61F 13/00* (2006.01)

(52) U.S. Cl.
CPC .......... *A61M 1/009* (2014.02); *A61M 1/0027* (2014.02); *A61M 1/0088* (2013.01); *A61F 2013/00174* (2013.01); *A61F 2013/00536* (2013.01); *A61M 2205/3344* (2013.01)

(56) References Cited

U.S. PATENT DOCUMENTS

| | | | | |
|---|---|---|---|---|
| 6,613,953 | B1* | 9/2003 | Altura | A61F 7/02 602/41 |
| 8,439,894 | B1* | 5/2013 | Miller | A61F 13/00068 604/313 |
| 2002/0156410 | A1* | 10/2002 | Lawry | A61F 5/055 602/18 |
| 2003/0212350 | A1* | 11/2003 | Tadlock | A61H 9/005 601/2 |
| 2005/0113732 | A1 | 5/2005 | Lawry | |
| 2008/0103462 | A1* | 5/2008 | Wenzel | A61F 13/023 604/313 |
| 2008/0167593 | A1 | 7/2008 | Fleischmann | |
| 2008/0171958 | A1* | 7/2008 | Gundersen | A61F 13/0206 602/56 |
| 2009/0275922 | A1 | 11/2009 | Coulthard et al. | |
| 2009/0293887 | A1* | 12/2009 | Wilkes | A61L 15/60 128/888 |
| 2009/0299303 | A1 | 12/2009 | Seegert | |
| 2010/0260824 | A1* | 10/2010 | Shah | A01N 25/00 424/447 |
| 2010/0305524 | A1* | 12/2010 | Vess | A61M 1/0023 604/313 |
| 2011/0015560 | A1 | 1/2011 | Marasco | |
| 2011/0245788 | A1 | 10/2011 | Marquez Canada | |

OTHER PUBLICATIONS

Search Report of counterpart European Patent Application No. 13706673.4 dated Dec. 20, 2016.
Search report of counterpart British Patent Application No. 1201698.6 dated Apr. 24, 2012.
Search report of counterpart British Patent Application No. 1201698.6 dated Jan. 20, 2017.

* cited by examiner

SCAR REDUCTION APPARATUS

The present invention relates to scar reduction apparatus, and more particularly to such apparatus which applies a positive pressure to a patient's scar area using evacuation to prevent, limit or reduce adverse scarring.

There is a number of known pieces of prior art which suggest various devices for application to a wound site. However, none of these utilise or are suitable for applying a compressive force via evacuation to a scar tissue site in order to prevent, limit or reduce hypertrophy of scar tissue.

US20100249688A1 utilises a sponge element, referred to as 'scaffold', for placement within a fresh open wound and evacuation to impart a reduced pressure whereby wound fluids are sucked out of the open wound site. Evacuation is not used to impart a positive compressive force to scar tissue via the sponge element.

U.S. Pat. No. 7,683,234B2 discloses a device for controlling or regulating the mechanical environment of a wound to ameliorate scar and/or keloid formation. However, this device is largely similar to a bandage or plaster and is used to cover the wound site so as to prevent or limit undue stress across the forming scar. No evacuation is utilised to impart a positive pressure to the scar site.

WO2008063281A1 only suggests a vacuum dressing for covering and closing off a wound site. This device is not intended to and will not prevent, limit or reduce scar hypertrophy. The vacuum is applied directly to the wound site, and there is no interior compressible pressure element for asserting a substantially uniform positive force onto the scar site.

EP1578477B1 relates primarily to post-operative fluid control and drainage following closure of separated tissue, for example, after a medical procedure. A vacuum source is utilised to extract fluid through a pressure-collapsible foam element. However, this device is not suitable for treatment of a scar site as a predetermined uniform or substantially uniform compression related to the application of a specific pressure cannot be achieved. Furthermore, collapsing of the foam element occurs in all directions, potentially leaving areas of the wound exposed.

The present invention seeks to provide a solution to these problems, thereby enabling specific post-scar formation treatment of a wound site.

According to a first aspect of the invention, there is provided Scar reduction apparatus comprising: a biocompatible scar interface layer; a compressible pressure chamber which at least substantially overlies the scar interface layer; a uniformly or substantially uniformly compressible pressure element in the pressure chamber and extending over at least a majority of the scar interface layer, the pressure element having a bulk modulus enabling a predetermined uniform or substantially uniform compression of the pressure element in at least a direction perpendicular or substantially perpendicular to the scar interface layer on application of a specific pressure; evacuation means for at least partially evacuating the pressure chamber, whereby the pressure element is uniformly or substantially uniformly compressed in the direction of the scar interface layer and the pressure chamber positively urges the compressed pressure element towards the scar interface layer; and a non-invasive connector which is spaced from a central region of the scar interface layer and which is at or adjacent to at least a perimeter of the scar interface layer for holding the scar interface layer in position over a user's scar.

According to a second aspect of the invention, there is provided a method of reducing scar tissue prominence, the method comprising the step of imparting a localised positive urging force directly to formed scar tissue via a uniformly or substantially uniformly localised negative pressure differential above the scar tissue.

The invention will now be more particularly described, by way of example only, with reference to the accompanying drawings, in which.

Figure 1:
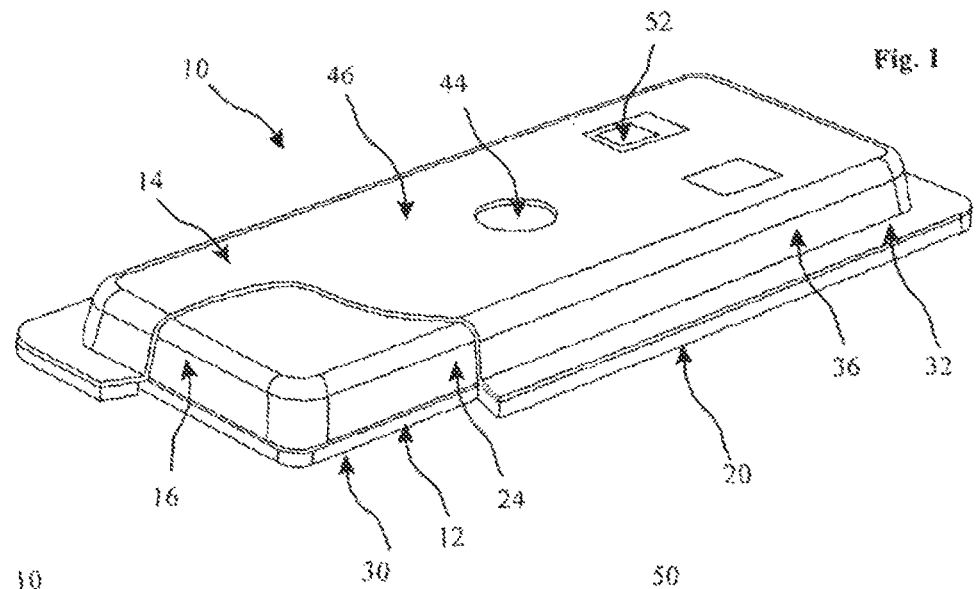
FIG. 1 is a partial cross-sectional perspective view of part of a first embodiment of scar reduction apparatus, in accordance with the first aspect of the invention.

Referring firstly to FIGS. 1 to 4b of the accompanying drawings, there is shown a first embodiment of scar reduction apparatus 10 which comprises a scar interface layer 12, a pressure chamber 14, a pressure element 16 within the pressure chamber 14, an evacuator 18 for evacuating the pressure chamber 14, and a non-invasive connector 20 for non-invasively attaching the apparatus 10 to a patient 22.

The scar interface layer 12 is a preferably smooth planar pliantly-flexible sheet of biocompatible material. Although other biocompatible materials can be considered, silicone is primarily advantageous as it has hypertrophic scar tissue reduction characteristics. A silicone gel sheet may be the preferred option for the apparatus 10. Other possible biocompatible materials that could be considered would, but not necessarily exclusively, be polyurethane foam, hydrogel sheet and/or hydrocolloid layers.

The scar interface layer 12 is also preferably fluid impermeable or occlusive, as this aids in isolating the interior 24 of the pressure chamber 14, thus potentially allowing the apparatus 10 to be reused rather than being disposable. However, the scar interface layer 12 may only be liquid impermeable whilst allowing gas or air flow therethrough for breathability. Alternatively, the scar interface layer 12 may be at least in part permeable, dependent on requirements.

In this embodiment, the scar interface layer 12 is rectangular, but other shapes being circular, non-circular or customised to specific anatomical features can be considered as necessity dictates.

The scar interface layer 12 is also preferably at least substantially non-adhesive. Having a non-adhesive interface is advantageous in allowing unhindered removal of the apparatus 10 from the patient 22, and especially from the scar site 26. However, in some situations, it may be beneficial to have a scar-interface layer which is at least substantially adherable to or adjacent to the scar tissue 28. In this latter case, this would be beneficial in preventing or limiting stress being imparted to the patient's scar tissue 28, for example, when undergoing a difficult healing process or where the original skin tissue or scar tissue 28 itself is particularly weak.

The pressure chamber 14 at least substantially overlies the scar interface layer 12, and in this embodiment fully overlies the scar interface layer 12 extending beyond the perimeter edge 30 of the scar interface layer 12 to provide a continuous outwardly projecting flange 32. So that the pressure chamber 14 is compressible, it is formed of a fluid impermeable pliantly-flexible sheet material, such as bio-compatible polymers, examples of which are polyurethane (polyether or polyester), Polyethylene, Ethylene Methyl Acrylate (EMA) and Polyvinylidene fluoride (PVDF) films or other suitable, preferably biocompatible, material.

The scar interface layer 12 may close a bottom of the pressure chamber 14, for example, by being bonded thereto at and/or adjacent to its perimeter edge 30. Alternatively, an interior 24 of the pressure chamber 14 may be isolated from the scar interface layer 12, and as such the scar interface layer 12 is connected to a bottom surface 34 of the pressure chamber 14, for example, by bonding.

Whether the pressure element 16 is seated directly on the scar interface layer 12 or whether it is fully encapsulated by the pressure chamber 14, the pressure element 16 extends over at least a majority of the scar interface layer 12, and is compressible by collapsible side walls 36 of the pressure chamber 14.

It is important that the pressure element 16 has a bulk modulus which enables a predetermined uniform or substantially uniform compression of the pressure element 16 in a direction which is perpendicular or substantially perpendicular to the scar interface layer 12 to be imparted on application of a specific known pressure. It is most preferable that the pressure element 16 undergoes no or limited compression in a direction parallel or substantially parallel to the scar interface layer 12, so that the extent of coverage of the pressure element 16 relative to the scar interface layer 12 is largely unaffected.

When applying a positive pressure to the scar site 26, the pressure should be uniform or substantially uniform over the entirety of the scar tissue 28, to prevent or limit the possibility of discoloration and/or unevenness. Consequently, the bulk modulus of the pressure element 16 enabling uniform or substantially uniform compression over the entirety of the pressure element 16 in the direction of the scar interface layer 12 is crucial. Furthermore, by utilising a pressure element 16 which has no or limited compression during evacuation in the direction parallel to the scar interface layer 12 allows a maximum possible area of the scar site 26 to be treated, thus allowing material usage of the apparatus 10 to be optimised.

Beneficially, the pressure element 16 is preferably a polymeric mesh material, such as a three-dimensional spacer fabric. Such a material is knitted XD Spacer fabric manufactured by Baltex® of Burr Lane, Ilkeston, United Kingdom or 3 mesh spacer fabric manufactured by Mueller Textile Group of Industriestrasse 8, Wiehl, Germany. The pressure element 16 provides a consistent and replicable positive pressure to the scar interface layer 12 on the imparting of a known specific negative pressure to the pressure chamber 14. Dependent on specific patient requirements, a physician can thus apply a known positive pressure to the whole of the patient's scar tissue 28 based on a known amount of evacuation of the pressure chamber 14.

Alternatively the pressure element could be constructed from a polymeric foam which has an open pore structure such as a reticulated polyurethane foam, an example of which is produced by Fritz Nauer AG of Oberwolfhauserstraße 9, CH-8633 Wolfhausen, Switzerland.

Another alternative for the manufacture of the pressure element is a customised injection moulding or extrusion forming a lattice or honeycomb shape. The advantage of this construction technique is that the collapsing force and direction can be precisely controlled by careful moulding design and material selection. Suitable materials for this moulding could include silicone, Thermoplastic Polyurethane (TPU) and Polypropylene.

Figure 2:
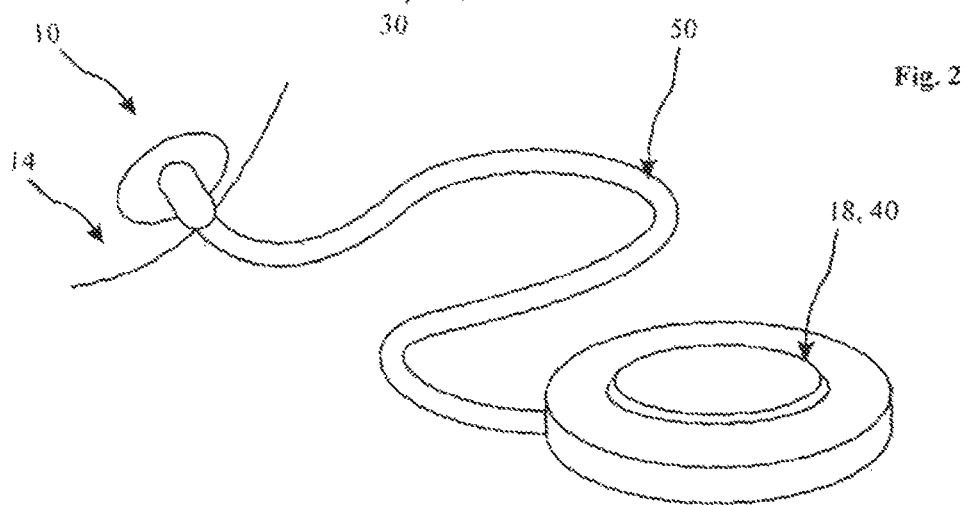
FIG. 2 is a perspective view showing an evacuator of the scar reduction apparatus, omitted from FIG. 1.
Figure 3:
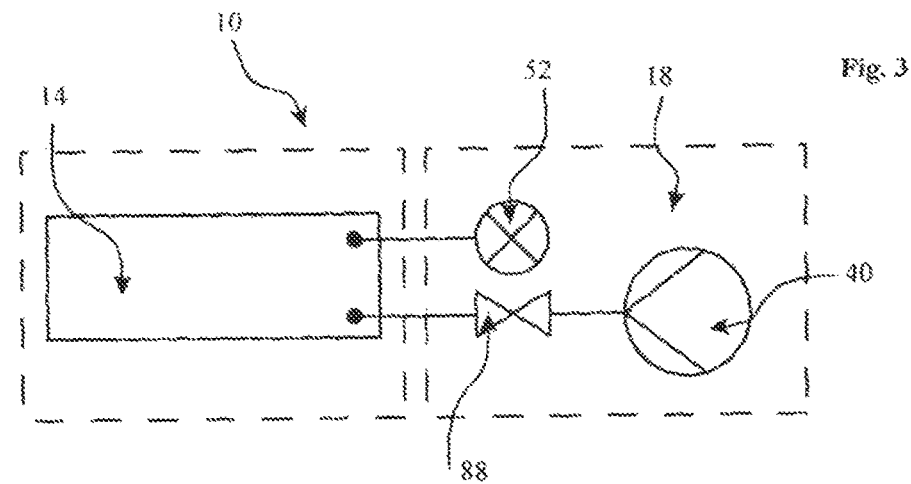
FIG. 3 is a generalised circuit diagram of the scar reduction apparatus, shown in FIGS. 1 and 2.
Figure 5:
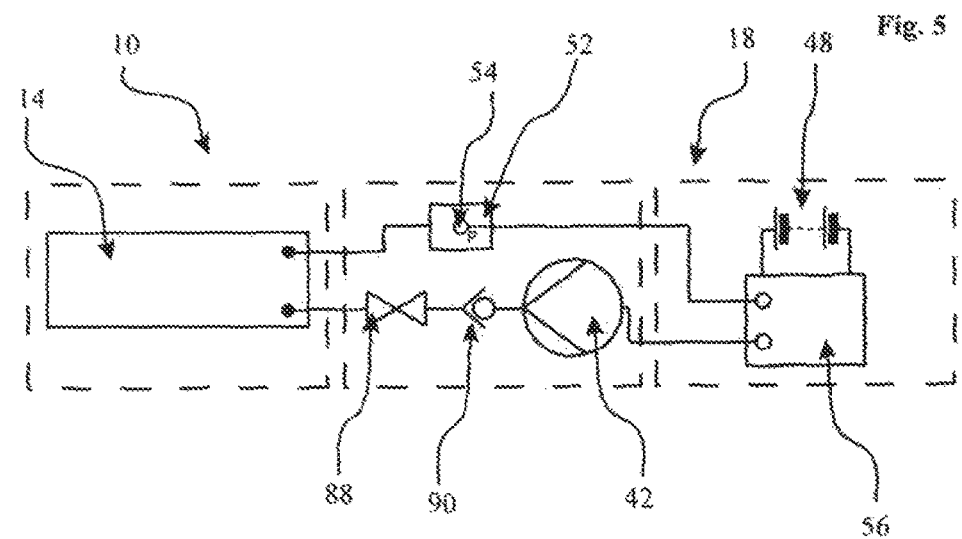
FIG. 5 is a generalised circuit diagram of a second embodiment of scar reduction apparatus, in accordance with the first aspect of the invention and showing an electrically operable evacuator.

The evacuator 18 may be a manual mechanical device 40, as shown in FIGS. 2 and 3, or may be an electrically driven device 42 as shown by the second embodiment of scar reduction apparatus 10 in FIG. 5. The manual mechanical device 40 may be, by way of example only, a syringe or a dedicated pump. The electrically driven device 42 may advantageously be a micro-pump, such as a piezo-electric pump. Such a piezo-electric pump is produced by Bartels Mikrotechnik GmbH of Emil-Figge-Str. 76a, D-44227 Dortmund, Germany. Other conventional miniature pumps can also be considered, such as a TCS D200 series pump available from TCS Micro Ltd of Highfield, Faversham Road, Kent, United Kingdom.

Preferably, the evacuator 18 may be an on-board vacuum device, for example, located on a fluid flow port 44 in an upper surface 46 of the pressure chamber 14. If electrically operable, then a suitably sized battery 48, such as a Lithium Ion battery, or other long life onboard power supply would also be mounted on the pressure chamber 14. This thus enables the scar reduction apparatus 10 to be an integrated standalone unit.

In the alternative and as shown in FIG. 2, the evacuator 18 may be a remote device tetherable to the fluid flow port 44 on the pressure chamber 14 via a fluid flow conduit 50. In this case, the evacuator 18 and/or the fluid flow conduit 50 would be preferably disconnectable from or adjacent to the fluid flow port 44.

The apparatus 10 may further comprise an interior-pressure indicator 52 for indicating a pressure set by the evacuator 18 in the pressure chamber 14. The interior-pressure indicator 52 may be integrated as part of the evacuator 18, or may be separate. Preferably, the interior-pressure indicator 52 is provided on a wall 36 or upper surface 46 of the pressure chamber 14, thereby allowing a physician or patient 22 to determine the pressure set by the evacuator 18.

The interior-pressure indicator 52 may be a visual gauge and/or audible signal, and may be settable to a required predetermined interior 24 pressure.

Additionally, the apparatus 10 may further include a pressure variance indicator 54 for indicating a variation of a set pressure in the pressure chamber 14. This may conveniently be integrated as part of the interior-pressure indicator 52, or may be a separate monitoring unit. In both cases, the pressure variance indicator 54 is preferably mounted on the upper surface 46 or side wall 36 of the pressure chamber 14, and beneficially provides a visual and/or audible alert if the pressure within the pressure chamber 14 increases beyond that set by the interior-pressure indicator 52.

In the case of an electrically operable evacuator 18, interior-pressure indicator 52 and pressure variance indicator 54, it may be advantageous to provide an electronic controller 56 for automatically controlling and regulating the evacuator 18 and thus pressure within the pressure chamber 14 based on a user setting of the interior-pressure indicator 52 and feedback from the pressure variance indicator 54.

A typical pressure required within the pressure chamber to collapse it will be in the order of 100 mmHg to 300 mmHg and this will produce an external force in the range of 10N to 20N as pressure chamber 14 tries to expand and provides a positive force on the scar interface layer 12.

In some cases it may be beneficial to pre evacuate the pressure chamber 14 using the evacuator 18 and seal the chamber 14 by means of a stop valve (not shown). The evacuator could then be disconnected from the apparatus 10. The apparatus 10 can then be secured to the patient's skin by non-invasive connector 20 or held in place with external tape, drape or other fixation method extending from the top of the collapsed pressure chamber 14 directly onto the patient's skin.

If the stop valve is opened, then the pressure chamber 14 will provide a positive force on the scar interface layer 12 due to the pressure element 16 returning to its pre-evacuated state and reacting by the connector 20 or external tape fixation. Additionally, the stop valve may include a pressure relief valve to control the rate at which the apparatus expands.

The non-invasive connector 20 extends solely and continuously around the scar interface layer 12 at or adjacent to the perimeter thereof. In this embodiment, the non-invasive connector 20 is a biocompatible adhesive strip, for example a Medical Grade double sided tape such as MED 1834 manufactured by Avery Dennison Medical Solutions of Tieblokkenlaan 1, B-2300 Turnhout, Belgium which is provided continuously on the underside of the outwardly extending flange 32 of the pressure chamber 14.

The non-invasive connector 20, in this case, preferably does not extend onto a central region 58 of the scar interface layer 12. It is generally important that the non-invasive connector 20 does not affect the positive pressure set by the apparatus 10 and being applied to the scar tissue area. In some instances it may be beneficial to apply additional securing means for holding the apparatus 10 to the patient's skin, such as an overlying medical drape or biocompatible medical tape. An example of which could be a single coated polyurethane film, such as MED 5021 manufactured by Avery Dennison Medical Solutions of Tieblokkenlaan 1, B-2300 Turnhout, Belgium. Alternative medical grade tapes and/or films could be used provided they were suitable for prolonged attachment to intact skin such as 3M® Transpore® surgical tape or 3M® Micropore® Medical tape manufactured by 3M of St. Paul, Minn. 55144-1000, United States.

The non-invasive connector 20 should also not puncture the patient's skin, for example, by the use of stitches. This creates further scarring.

Figure 4A:
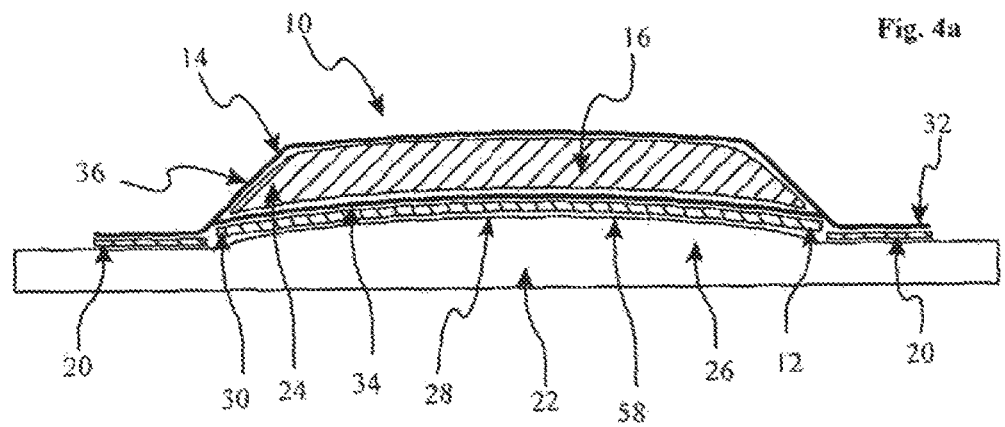
FIG. 4a shows the first embodiment of the scar reduction apparatus in top-to-bottom cross section, when in use, with the evacuator omitted for clarity and in a non-evacuated condition.
Figure 4B:
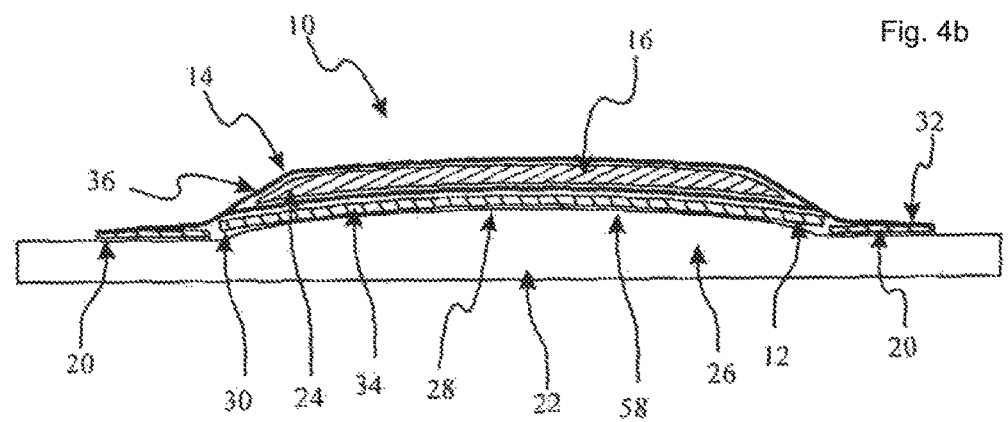
FIG. 4b is similar to FIG. 4a, showing a cross-section of the in use scar reduction apparatus, in an evacuated condition.

In use, the scar interface layer 12 of the apparatus 10 is placed directly into contact with the patient's scar tissue 28, as shown in FIG. 4a. Typically, the scar tissue 28 will be formed such that the wound is closed and sealed, and the scar will be at least in part hypertrophic or keloidal. The apparatus 10 is held in place over the scar site 26 by the non-invasive connector 20. The evacuator 18 is operated, either manually or electrically as described above, to at least partially evacuate the pressure chamber 14 to the required negative pressure, monitored by the interior-pressure indicator 52. The partial evacuation causes the pressure chamber 14 to collapse onto and around the pressure element 16. The known bulk modulus of the pressure element 16 and the compression characteristics causes the pressure element 16 to be at least substantially uniformly compressed in the direction of the scar interface layer 12 with minimal or no compression parallel to the scar interface layer 12, thereby at least substantially maintaining the original coverage of the scar site 26 by the pressure element 16.

It is generally understood that a prolonged positive pressure of as little as 15 mmHg can affect a positive scar response in terms of reduced hypertrophy. Additional in vitro studies have shown that compression pressure of 35 mmHg for twenty four hours can induce apoptosis and regulate cytokine release in hypertrophic scars, which may regress scar formation. Consequently, the apparatus 10 of the present invention is adapted to preferably impart selectable pressure up to 100 mmHg and the pressure element is selected accordingly. The required positive pressure is achievable by monitoring the pressure within the pressure chamber 14 and/or the exterior/interior pressure differential along with knowing the compression characteristics of the pressure element 16 leading to a positive determinable specific downward pressure being imparted to the scar interface layer 12, and thus in turn to the scar tissue 28.

The interior pressure of the pressure chamber 14 is monitored by the pressure variance indicator 54, and as such deviation from the set internal pressure can be corrected via the evacuator 18.

Figure 6:
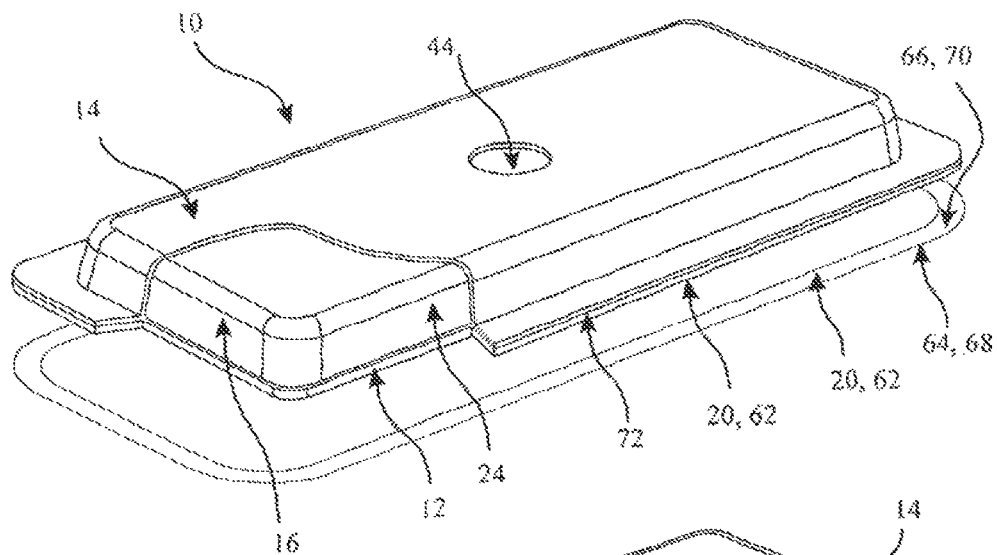
FIG. 6 is a partial cross-sectional perspective view of part of a third embodiment of scar reduction apparatus, in accordance with the first aspect of the invention and utilising a separable two part scar interface layer.

Referring now to FIG. 6, a third embodiment of scar reduction apparatus 10 is shown. Like references refer to parts which are the same as or similar to those of the first embodiment, and therefore further detailed description is omitted.

The apparatus 10 of this embodiment again comprises the scar interface layer 12, pressure chamber 14, pressure element 16, evacuator 18 and non-invasive connector 20. However, in this case, the non-invasive connector 20 includes two separable layers 60, 62.

A first lower layer 60 of the non-invasive connector 20 is skin contactable and includes a skin-adherable base layer 64 and an upper connector layer 66. The skin-adherable base layer 64 is skin contactable and preferably is or includes therefore a biocompatible adhesive 68. The upper connector layer 66 is superposed on or above the skin-adherable base layer 64, and includes a re-usable and releasable adhesive 70. The first lower layer 60 therefore defines a continuous ring which is complimentarily shaped to match the second upper layer 62 of the non-invasive connector 20 residing on the outwardly extending flange 32 of the pressure chamber 14.

The second upper layer 62 also comprises a re-usable and releasable adhesive 72 which can be releasably engaged with the re-usable and releasable adhesive 70 of the upper connector layer 66.

Consequently, the first ring-like lower layer 60 of the non-invasive connector 20 can be applied around the scar site 26 and held in place by the biocompatible skin-adherable base layer 64. The second upper layer 62 of the non-invasive connector 20, together with the scar interface layer 12, pressure chamber 14 and pressure element 16 therein, can then be releasably mounted to the upper connector layer 66 as an integral unitary module. As such, the scar interface layer 12, pressure chamber 14 and pressure element 16 can be removed and reapplied as necessity dictates, for example, in order to examine the scar tissue 28, without having to remove the first lower layer 60 of the non-invasive connector 20 interfacing with the patient's skin.

In a modification to the third embodiment, the scar interface layer 12 may include two releasably engagable layers. In this case, the non-invasive connector 20 is provided continuously at and/or adjacent to the perimeter edge 30 on a lower surface of a first lower layer of the scar interface layer 12. A re-usable and releasable adhesive is provided, preferably continuously, at and/or adjacent to the perimeter edge 30 on an upper surface of the first lower layer. A complimentary re-usable and releasable adhesive is also provided on the outwardly extending flange 32 of the pressure chamber 14. The pressure chamber 14 is closed by a second upper layer of the scar interface layer 12, although in this case, the second upper layer may not need to be biocompatible if it does not contact the patient's skin.

Consequently, the first lower layer can be applied to the scar site 26 and held in place by the non-invasive connector 20. The second upper layer of the scar interface layer 12, along with the interconnected pressure chamber 14 housing the pressure element 16, can then be releasably mounted to the first lower layer. The pressure chamber 14 and pressure element 16 can thus be removed as an integrated unit, for example, for replacement, without requiring removal of the first lower layer of the scar interface layer 12 from direct contact with the patient's skin.

Figure 7:
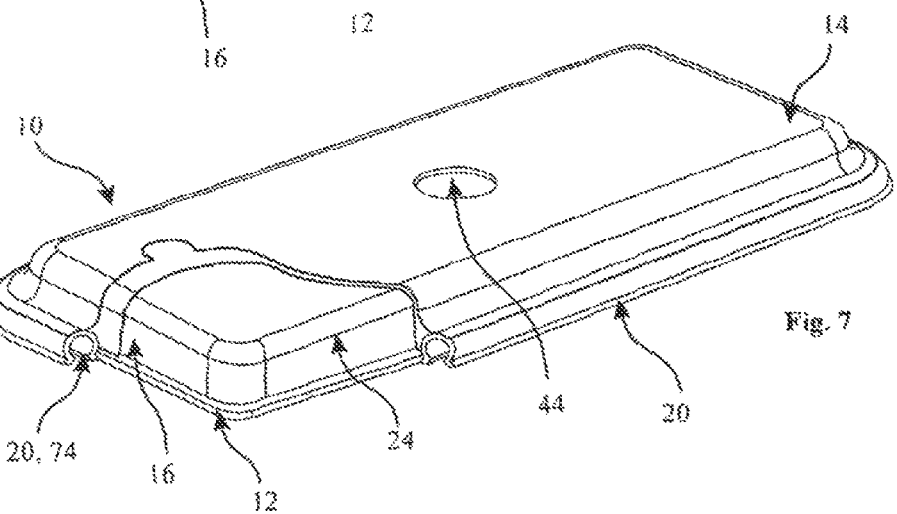
FIG. 7 is a partial cross-sectional perspective view of part of a fourth embodiment of scar reduction apparatus, in accordance with the first aspect of the invention and utilising a vacuum-operable non-invasive perimeter connector.
Figure 8:
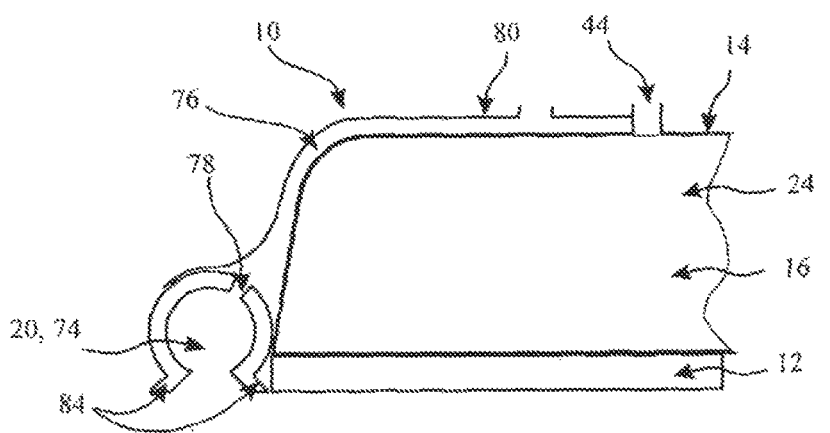
FIG. 8 is an enlarged view of part of the vacuum-operable non-invasive perimeter connector, shown in FIG. 7.
Figure 9:
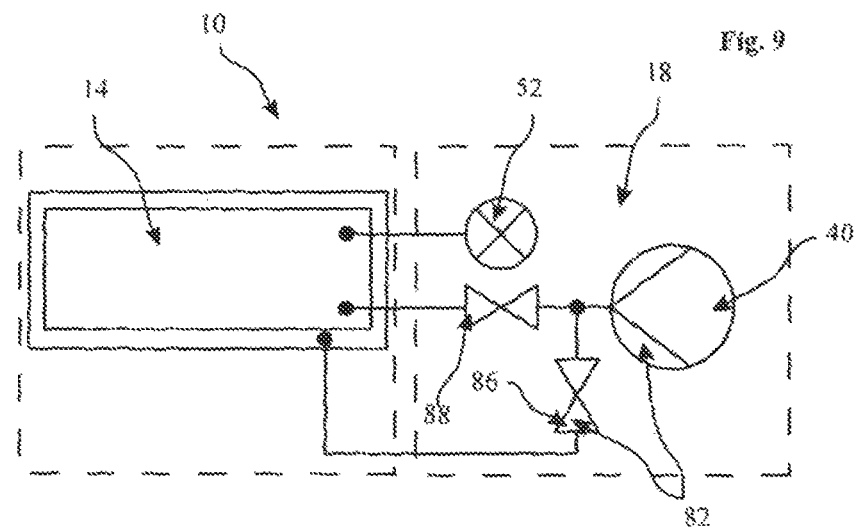
FIG. 9 is a generalised circuit diagram of the fourth embodiment of scar reduction apparatus.

Referring now to FIGS. 7 to 9, a fourth embodiment of scar reduction apparatus 10 is shown. Like references refer to parts which are the same as or similar to those of the first embodiment, and therefore further detailed description is omitted.

The apparatus 10 of this embodiment again comprises the scar interface layer 12, pressure chamber 14, pressure element 16, evacuator 18 and non-invasive connector 20. However, in this case, the non-invasive connector 20 is vacuum operable instead of utilising adhesive.

The non-invasive connector 20 of this embodiment comprises a channel connector element 74 connected to an outer surface 76 of the pressure chamber 14. The channel connector element 74 extends continuously around a perimeter of the pressure chamber 14, and as such the outwardly extending flange 32 of the first embodiment may be dispensed with.

Apertures 78 in upper portions of the channel connector element 74 are in fluid communication with a manifold 80 covering the pressure chamber 14, as best seen in FIG. 8. A further evacuator 82, as diagrammatically depicted in FIG. 9, is utilised to evacuate the manifold 80 and thus the channel connector element 74, causing vacuum or suction engagement with the patient's skin.

To further promote maintenance of the vacuum engagement, depending free edges of the channel connector element 74 may each include a flexible continuous skirt 84.

The further evacuator 82 preferably forms part of the first said evacuator 18 described with reference to the first embodiment. In this case, the further evacuator 82 utilises a separate valve 86 to enable control of the suction and a pump or air extraction device which is common to the first and second said extractors 18, 82. In this case, a further valve 88 may be incorporated as part of the said first extractor 18 to also allow specific control of the evacuation of the pressure chamber 14, whereby independent or simultaneous evacuation of the channel connector element 74 and/or the pressure chamber 14 can be undertaken. A check valve 90 may also be utilised as required.

Additionally, the continuous skirt 84 may be omitted in some configurations and the manifold 80 and channel connector 76 may thus be extended directly to the patient's skin and adhered utilising a Medical Grade double sided tape, such as MED 1834 manufactured by Avery Dennison Medical Solutions of Tieblokkenlaan 1, B-2300 Turnhout, Belgium.

Figure 10:
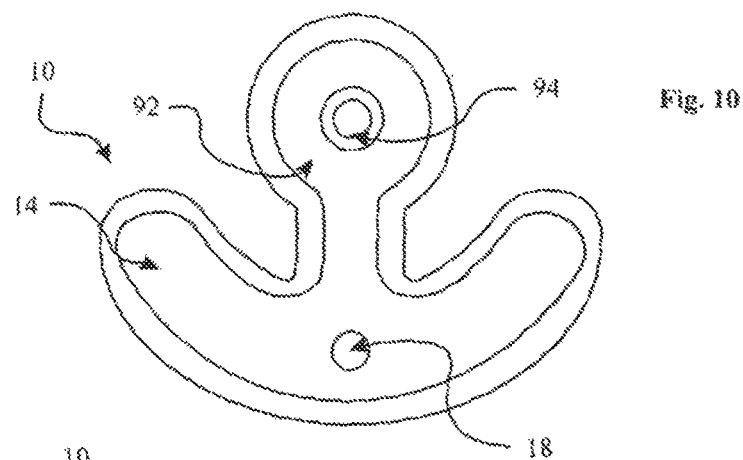
FIG. 10 is a front elevational view of a fifth embodiment of scar reduction apparatus, in accordance with the first aspect of the invention and specifically adapted for a scar site on a female patient's breast.
Figure 11:
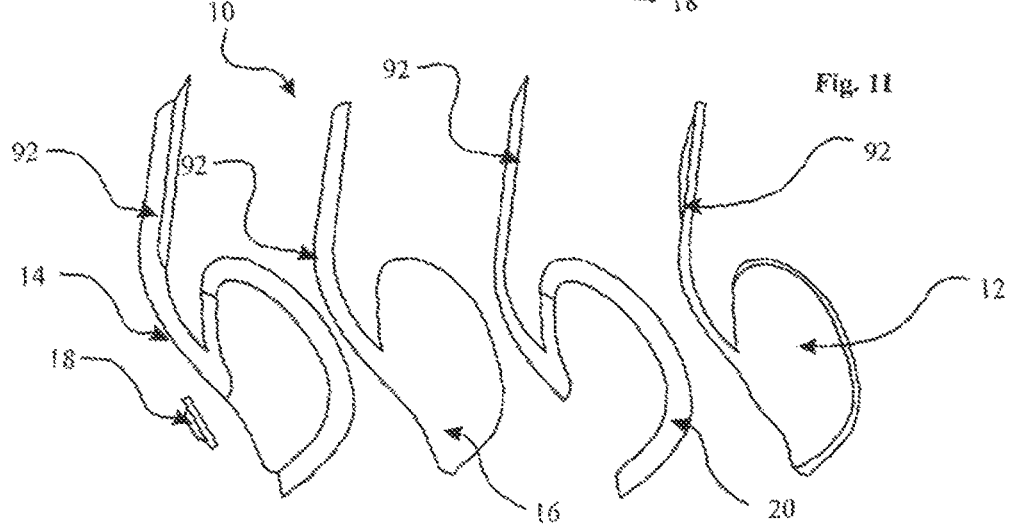
FIG. 11 is an exploded side view of the scar reduction apparatus shown in FIG. 10.

Referring now to FIGS. 10 and 11, a fifth embodiment of scar reduction apparatus 10 is shown. Again, like references refer to parts which are the same as or similar to those of the first embodiment, and therefore further detailed description is omitted.

The apparatus 10 of this embodiment comprises the scar interface layer 12, pressure chamber 14, pressure element 16, evacuator 18 and non-invasive connector 20. In this case, the apparatus 10 is anatomically profiled to match or substantially match a curvature of a user's body part. In particular, the embodiment shown in FIGS. 10 and 11 is adapted for a female patient's breast and includes a protruding location element 92 which in this case provides a nipple aperture 94 for receiving a user's nipple. The protruding location element 90 is provided by the shaping of the scar interface layer 12, pressure chamber 14, pressure element 16 and the non-invasive connector 20. The protruding location element 90 therefore prevents or inhibits the apparatus 10 from unintentionally disengaging from the scar site 26.

The aforedescribed evacuator may be any suitable evacuation means, and when in the form of a manual evacuator may be incorporated as part of and/or on-board with the pressure chamber. In this case, the evacuator relies on manual pressure being exerted to compress the pressure chamber and/or the pressure element by a user or carer and, for example, a stop valve or check valve on the pressure chamber allowing expulsion of air whilst preventing re-ingress.

Additionally or alternatively, the evacuation operation can be undertaken prior to application of the apparatus to the user, or once application has taken place.

Furthermore, once applied in the compressed state, release of the pressure within the evacuated pressure chamber provides the required positive force on the scar interface layer due to the pressure element returning to its pre-evacuated state and reacting against the connector or external tape fixation.

Although a pressure relief valve is suggested in order to control the rate at which the apparatus expands, any suitable flow control means can be utilised.

A re-sealable tab or flap may be positioned above an aperture or orifice in the pressure chamber film or wall. Opening the flap allows air to enter the evacuated chamber causing the pressure element to expand thus creating the required force. The re-sealable tab or flap can then be re-sealed and the chamber recharged or re-evacuated using any of the evacuation means herebefore described, as required. An example of a suitable material that could be used to produce the re-sealable tab or flap is manufactured by Steratape, UK, code number 4503F, which comprises of a permanent/peelable two sided carrier based tape with one side having a permanent adhesive onto a liner and the other side a peelable acrylic adhesive.

It is therefore possible to provide scar reduction apparatus which utilises differential pressure to impart a positive force to a biocompatible material in direct connect with existing scar tissue. This improves the appearance of the scar, and in particular a scar which is hypertrophic or keloidal. Pressure bandages are well known and apply force to the scar tissue by the use of elastic materials encircling the body part. However, in many cases, it is not only unfeasible to wrap the patient's body, but it is also highly uncomfortable along with the fact that elastic materials change their elastic properties over a short span of time, leading to pressure variance. The apparatus of the present invention does not require encircling of the body part, and is not elasticised. The apparatus is compact and sized to the patient's scar site, allowing the patient to easily conceal the apparatus beneath clothing. It is also possible to provide scar reduction apparatus which minimises damage and stress imparted to surrounding tissue. Furthermore, it is possible to provide apparatus which can apply a predetermined uniform or substantially uniform compression to the scar tissue on application of a specific known pressure.

The embodiments described above are provided by way of examples only, and various other modifications will be apparent to persons skilled in the art without departing from the scope of the invention as defined by the appended claims.

The invention claimed is:

1. A post-scar formation reduction apparatus for post-scar formation treatment of a wound site, the apparatus comprising-:
   a biocompatible scar interface layer;
   a compressible pressure chamber which at least substantially overlies the scar interface layer;
   a uniformly or substantially uniformly compressible pressure element in the pressure chamber and extending over at least a majority of the scar interface layer, the pressure element having a bulk modulus enabling a predetermined uniform or substantially uniform compression of the pressure element in at least a direction perpendicular or substantially perpendicular to the scar interface layer on application of a specific pressure;
   an evacuator which at least partially evacuates the pressure chamber, whereby the pressure element is uniformly or substantially uniformly compressed in the direction of the scar interface layer and the pressure chamber positively urges the compressed pressure element towards the scar interface layer;
   a non-invasive connector which is spaced from a central region of the scar interface layer and which extends continuously around a perimeter of the scar interface layer for holding the scar interface layer in position over a user's scar, wherein the non-invasive connector is provided on one of an outwardly extending continuous flange or a flexible continuous skirt;
   wherein the scar interface layer is fluid impermeable.

2. The post-scar formation reduction apparatus as claimed in claim 1, wherein the scar interface layer at least includes silicone for reducing adverse scarring.

3. The post-scar formation reduction apparatus as claimed in claim 1, wherein the pressure element during evacuation of the pressure chamber is at least substantially non-compressible in a direction parallel or substantially parallel to the scar interface layer, so that the pressure element maintains the said at least majority coverage of the scar interface layer.

4. The post-scar formation reduction apparatus as claimed in claim 1, wherein the scar interface layer is at least substantially non-adhesive.

5. The post-scar formation reduction apparatus as claimed in claim 1, wherein the pressure element is or includes a compressible spacer element.

6. The post-scar formation reduction apparatus as claimed in claim 5, wherein the spacer element is at least one of a polymeric mesh block and polymeric foam.

7. The post-scar formation reduction apparatus as claimed in claim 1, wherein the evacuator relies on manual pressure to compress the pressure chamber and/or the pressure element.

8. The post-scar formation reduction apparatus as claimed in claim 1, further comprising a re-sealable tab or flap to allow air to enter the evacuated pressure chamber.

9. The post-scar formation reduction apparatus as claimed in claim 1, further comprising a valve which allows expulsion of air from the pressure chamber whilst preventing re-ingress into the pressure chamber.

10. The post-scar formation reduction apparatus as claimed in claim 1, wherein the non-invasive connector includes further evacuator comprising a perimeter skin-engagable suction channel and an outer skin manifold which overlies at least part of the pressure chamber.

11. The post-scar formation reduction apparatus as claimed in claim 1, wherein the non-invasive connector includes a separable skin-adherable base layer and an upper connector layer which is directly or indirectly connected to the scar interface layer and the pressure chamber, the upper connector layer being repeatedly demountably attachable to the base layer.

12. The post-scar formation reduction apparatus as claimed in claim 1, wherein said pressure chamber is at least in part pre-evacuatable prior to application to a user's scar, and the pre-evacuation is maintainable prior to said application.

13. A method of reducing scar tissue prominence, the method comprising the step of imparting a localised positive urging force directly to formed scar tissue via a uniformly or substantially uniformly localised negative pressure differential above the scar tissue, the negative pressure differential being imparted by an at least partially air-evacuated chamber above the scar tissue and wherein said chamber is at least partially air-evacuated prior to application above the scar tissue.

14. The method as claimed in claim 13, wherein the positive urging force is imparted by an at least partially compressed pressure element.

15. The method as claimed in claim 14, wherein the pressure element is at least partially compressed prior to application above the scar tissue.

16. The method as claimed in claim 13, wherein said chamber is at least partially air-evacuated subsequent to application above the scar tissue.

* * * * *